United States Patent [19]
Thomas et al.

[11] Patent Number: 5,269,771
[45] Date of Patent: Dec. 14, 1993

[54] NEEDLELESS INTRODUCER WITH HEMOSTATIC VALVE

[75] Inventors: Joseph J. Thomas, Berwyn; David G. Catlin, West Chester; Andrew Armour, Delaware County; Robert W. Thomas, Wayne, all of Pa.

[73] Assignee: Thomas Medical Products, Inc., Malvern, Pa.

[21] Appl. No.: 21,838

[22] Filed: Feb. 24, 1993

[51] Int. Cl.[5] .................. A61M 25/00; A61M 5/078
[52] U.S. Cl. .................... 604/213; 604/167; 604/256; 251/149.1
[58] Field of Search ............ 604/167, 164, 280, 283, 604/278, 256; 251/149.1; 137/854

[56] References Cited

U.S. PATENT DOCUMENTS

| | | | |
|---|---|---|---|
| 4,421,296 | 12/1983 | Stephens | 604/99 |
| 4,610,469 | 9/1986 | Wolff-Mooij | 604/411 |
| 4,684,364 | 8/1987 | Sawyer et al. | 604/247 |
| 5,009,391 | 4/1991 | Steigerwald | 604/167 |
| 5,062,836 | 11/1991 | Wendell | 604/167 |
| 5,064,416 | 11/1991 | Newgard et al. | 604/167 |
| 5,149,327 | 9/1992 | Oshiyama | 604/167 |
| 5,156,596 | 10/1992 | Balbierz et al. | 604/164 |
| 5,188,620 | 2/1993 | Jepson et al. | 604/283 |
| 5,195,980 | 3/1993 | Catlin | 604/167 |

Primary Examiner—John G. Weiss
Attorney, Agent, or Firm—Caesar, Rivise, Bernstein, Cohen & Pokotilow, Ltd.

[57] ABSTRACT

A needleless device for introducing or withdrawing a fluid to/from the vascular system of a being. The device includes first and second housing sections movably connected with respect to each other and which define a hollow interior in which a pair of resilient valve elements are located. The first housing section includes a first luer fitting for connection to an input line. The second housing section includes a second luer fitting for connection to an output line. A tubular plunger is located within the device and is arranged, when the housing sections are in a first position, to be automatically extended through a first valve element if the input line is connected to the first luer fitting, so that a liquid can be forced from the input line through the device to the output line. When the housing sections are in the first position and the input line disconnected from the first luer fitting, the tubular plunger is retracted out of both valve elements so that the device is fully occluded. The housing sections are movable to a second position with the input line connected to the first luer fitting, whereupon the tubular plunger is extended through both valve elements to provide free fluid communication between the input and output lines.

15 Claims, 4 Drawing Sheets

NEEDLELESS INTRODUCER WITH HEMOSTATIC VALVE

BACKGROUND OF THE INVENTION

This invention relates generally to medical devices and more particularly to needleless introducers including hemostatic valves.

Various valved connectors are disclosed in the U.S. patent literature to serve in supply lines for fluids supplied to or extracted from the vascular system of a living being. Examples of such patents are as follows: 4,421,296 (Stephens); 4,535,820 (Raines); 4,610,469 (Wolff-Mooij); 4,683,916 (Raines); 4,935,010 (Cox et al.); and 5,057,084 (Ensminger et al.). A valved medicine container for use in a needleless medication transfer system is disclosed in U.S. Letters Pat. No. 5,092,840 (Healy).

In a copending U.S. Pat. application Ser. No. 07/816,988, filed on Jan. 3, 1992, entitled Hemostatic Valve, which is assigned to the same assignee as this invention and whose disclosure is incorporated by reference herein there is disclosed a device for enabling the introduction of an elongated member, e.g., a balloon catheter, into the body of a living being while precluding blood from flowing out of the device. The device includes a housing having an interior in which a pair of resilient valve elements and a plunger mechanism are located. One valve element, e.g., a disk-like member, has a small diameter opening therein. The other valve element, e.g., a duck-bill valve element, includes a normally closed, but openable, aperture therein. The plunger mechanism includes a tubular member having an outer diameter which is smaller than the diameter of the opening in the one valve element. The tubular member is arranged to be moved into and out of the opening in the one valve member and into and out of the aperture in the other valve element. The tubular member has a central passageway arranged to enable the elongated member to be readily extended therethrough for location at a desired position within the body of the being. The one valve element is arranged for engaging the periphery of the elongated member after the elongated member has been extended through the passageway and after the tubular member is moved out of the opening in the valve member to preclude blood from flowing through the interface between the valve member and the elongated member.

As will be appreciated by those skilled in the art when access to the vascular system of a person is required, such as for infusing fluids or extracting (sampling) fluids therefrom, it is critical to avoid a needle-stick injury which could result in the transmission of AIDS or other blood-born infectious diseases, while maintaining control of bleeding and eliminating the possibility of an air embolism.

Prior art valved connectors or devices for use in vascular supply/sampling lines have not adequately addressed these needs heretofore.

OBJECTS OF THE INVENTION

Accordingly, it is a general object of this invention to provide an introducer including a hemostatic valve which overcomes disadvantages of the prior art.

It is a further object of this invention to provide an introducer for needleless vascular access, while obtaining complete hemostasis when no inlet connection exists.

It is still a further object of this invention to provide an introducer for needleless vascular access to effect injections, sampling, and gravity feed, with increased flow rates.

It is yet a further object of this invention to provide an introducer for needleless vascular access which prevents reflux caused by high pressure pulses from other injections sites.

It is yet a further object of this invention to provide a needleless introducer which is simple in construction.

SUMMARY OF THE INVENTION

These and other objects of this invention are achieved by providing an device for providing fluid access to a portion of the vascular system of a being. The device comprises housing means, valve means, and extendable plunger means. The housing means comprises a first housing section and a second housing section. The first housing section is coupled to the second housing section and is movable with respect to the second housing section from a first position to a second position and vice versa.

The first housing section comprises a first port for connection to an input line. The second housing section comprises a second port for connection to an outlet line in fluid communication with the portion of the being's vascular system. The housing sections define a hollow interior portion therebetween in which the valve means is located. The valve means comprises a first openable aperture and a second openable aperture.

The extendable plunger means comprises a tubular member movably coupled to the first housing section for extension through the first openable aperture in response to the input line being connected to the first port when the first housing section is in the first position, whereupon the a fluid may be forced from the input line through the tubular member and through the second openable aperture into the output line. The tubular member is retracted out of the first openable aperture in response to the disconnection of the input line from the first port, whereupon the first and second ports are isolated from each other by the valve means.

In accordance with one preferred aspect of this invention the movement of said first housing section to the second position with the input line connected to the first port causes the tubular member to extend through both of the openable apertures, whereupon the input and output ports are in fluid communication with each other via the tubular member to facilitate high flow rate feeding of a fluid into the being's vascular system or to enable the ready sampling of a fluid therefrom.

DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF THE PREFERRED EMBODIMENTS

Figure 1:
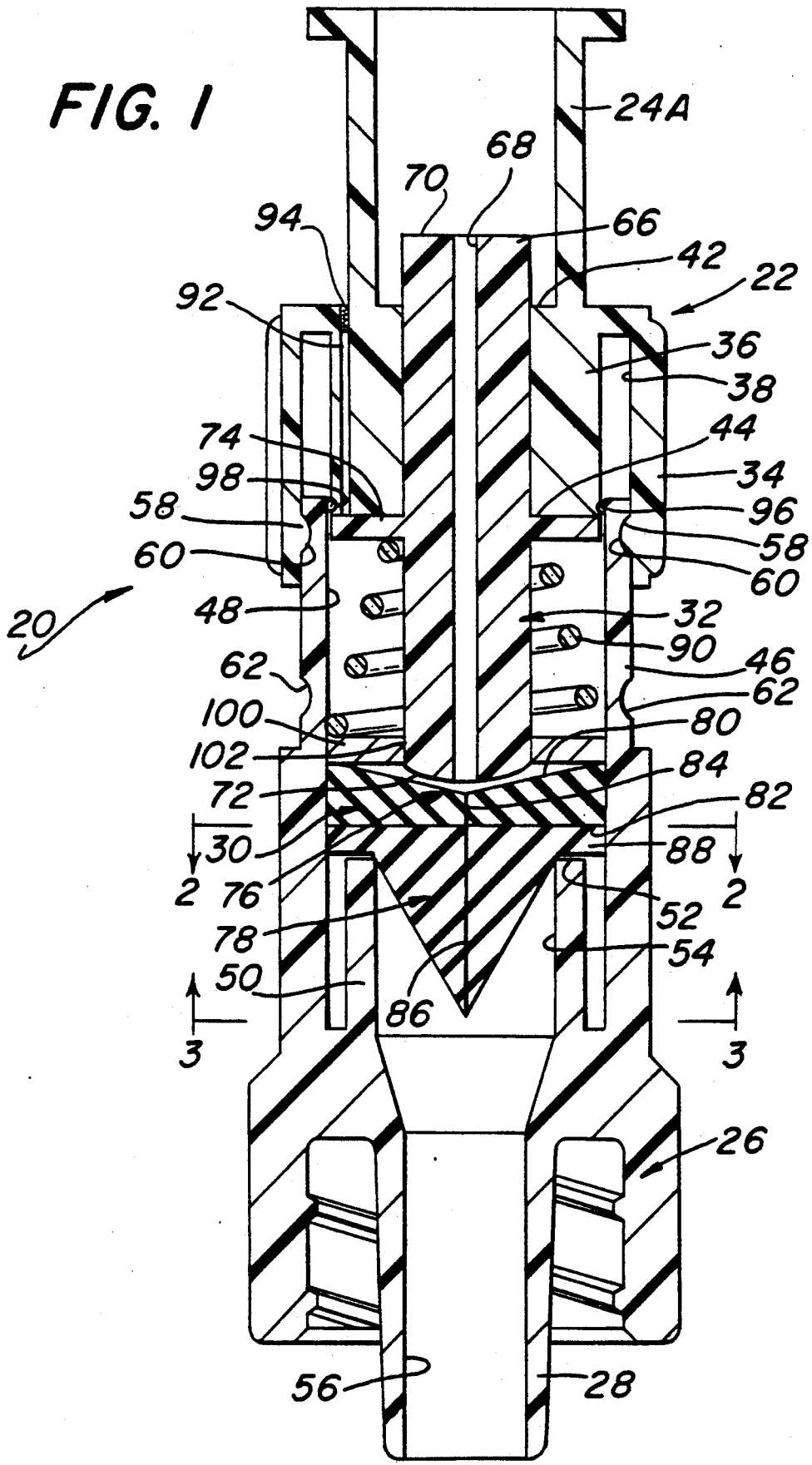
FIG. 1 is a longitudinal sectional view of a fluid line valve device constructed in accordance with this invention and shown in its fully closed state.
Figure 2:
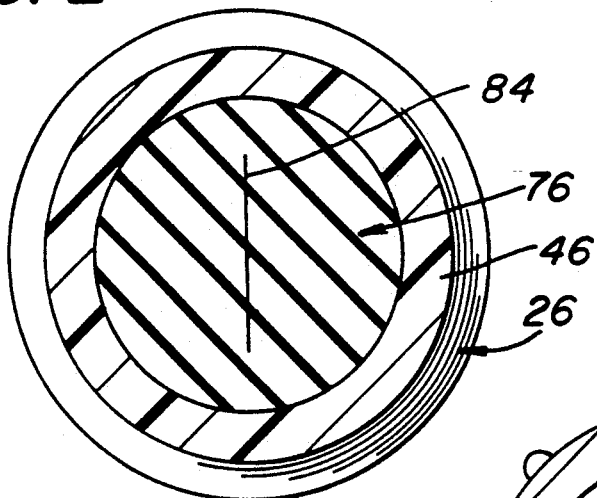
FIG. 2 is a sectional view taken along line 2—2 of FIG. 1.
Figure 3:
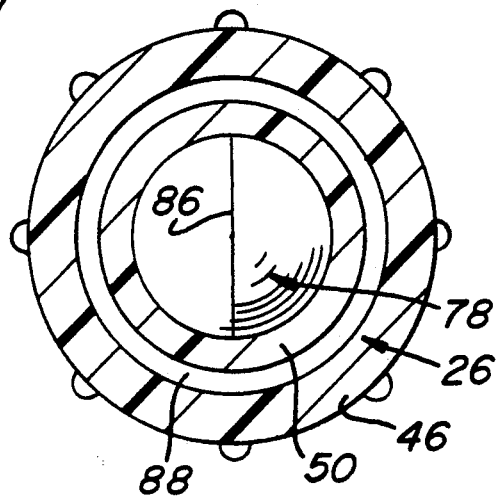
FIG. 3 is a sectional view taken along line 3—3 of FIG. 1.
Figure 5:
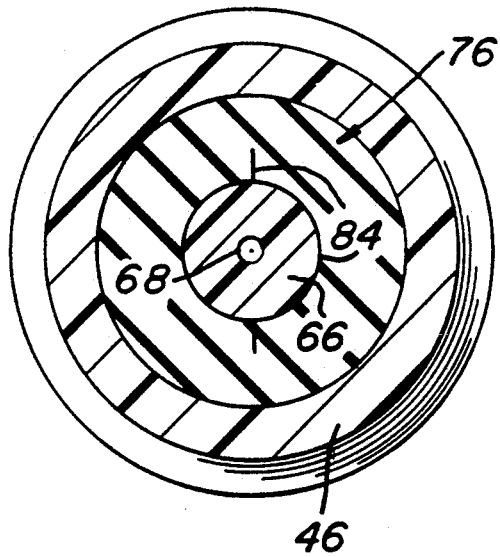
FIG. 5 is a sectional view taken along line 5—5 of FIG.
Figure 7:
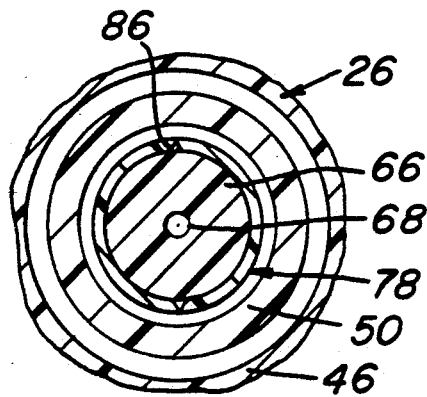
FIG. 7 is a sectional view taken along line 7—7 of FIG. 6.

Referring now to the various figures of the drawing wherein like reference characters refer to like parts, there is shown at 20 in FIG. 1, an fluid line valve device constructed in accordance with this invention. The fluid line device is includes an outlet port, e.g., a conventional male luer fitting, arranged to be connected to a mating female luer fitting (not shown) on the end of a line or conduit (not shown), having access to the vascular system of a living being to provide a fluid thereto or to extract a fluid therefrom. To that end the fluid line device 20 also includes an inlet port, e.g., a conventional female luer fitting, for receipt of a mating male luer fitting at the end of an input line which serves as a source of a fluid to be introduced or as a fluid sampling line. In particular, the device 20 of this invention is arranged so that when the input line is connected to the inlet port, valve means (to be described later) within the device are automatically partially opened by plunger means (also to be described later) so that a fluid can be forcibly introduced, e.g., injected, from the inlet line through the device into the being's vascular system, while providing reflux protection. Prior to connection of the input line to the inlet luer, the device is in its "neutral" position wherein the valve means within the device is completely occluded, thereby providing complete hemostasis as well as protection against an air embolism. The device 20 is adjustable so that it can be manually operated to move it from the neutral to an "actuated" position to cause the plunger means to fully open the valve means, thereby enabling the gravity feed of an infusion fluid or the injection of a fluid at higher flow rates through the device into the being's vascular system. In this fully opened or "actuated" condition the fluid line device 20 is suitable for ready sampling of a fluid from the being's vascular system. In all operating conditions the device 20 maintains control of bleeding, while eliminating the possibility of an air embolism.

Referring now to FIG. 1 it can be seen that the device 20 basically comprises a first housing section 22 having an input connector fitting 24A, a second housing section 26 having an output connector fitting 28, a valve assembly 30, and a spring- biased plunger assembly 32. The input fitting 24A is preferably a conventional female luer fitting arranged for connection to a mating male fitting 24B on an input line or conduit (not shown). The output fitting 28 is preferably a conventional male luer fitting arranged for connection to a mating female fitting (not shown), constructed like fitting 24A, on an I.V. output line or conduit (not shown) having access to the vascular system of the patient. The input line serves to provide a fluid, e.g., a liquid, from any suitable source, such as an injector (not shown) or a gravity feed bag (not shown) to the device from which passes through the valve assembly 30 via the plunger assembly 32 and from there through the output line into the patient's vascular system. The input line may also serve as the access line for withdrawing a fluid sample from the patient's vascular system via the valve assembly and plunger assembly.

The housing section 22 basically comprises a cylindrical member having the heretofore identified female luer fitting 24A at is proximal end and an annular sleeve 34 at it distal end. The housing section 22 also includes a cylindrical central core 36 located within the annular sleeve so that an annular space 38 is defined therebetween. The central core includes a central passageway 40 extending through it from the bottom 42 of the interior of the female luer fitting 24A to the distal end 44 of the core 36.

The housing section 26 also basically comprises a cylindrical member having an annular sleeve 46 at its proximal end and the heretofore identified male luer fitting 28 at is distal end. The interior of the sleeve 46 forms a cylindrical chamber 48 in which the valve assembly 30 and a portion of the plunger assembly 32 are disposed (as will be described later). The distal end of the chamber 48 includes an annular wall 50 whose proximal end face 52 serves as the seat for the valve assembly 30. A central passageway 54 extends through the distal end of the housing section 26 and communicates with the interior passageway 56 in the male luer fitting 28.

The two housing sections 22 and 26 are arranged to be releasably secured to each other in either the "neutral" or "activated" positions. In particular, the annular sleeve 46 of the housing section 26 is inserted into the annular recess 38 in the housing section 22 to releasably lock or snap-fit these sections together in either the "neutral" position or the "actuated" position. These positions are established by the coaction of a convex or rounded annular ridge 58 extending about the inner periphery of the annular sleeve 34 of the housing section 22 and respective ones of two complementary annular recesses 60 or 62 extending about the outer periphery of the annular sleeve 46 of the housing section 26. The recess 60 is located closely adjacent the proximal end of the annular sleeve 46, while the recess 62 is located a predetermined distance distally thereof.

When the annular ridge 58 of the housing section 22 is located within the annular recess 60 of the housing section 26 the device 20 is in the "neutral" position. In the neutral position if no input line is connected to the input female luer fitting 24A, such as shown in FIG. 1, the valve assembly 30 is fully closed so that the device 20 is totally occluded. In particular, and as will be described later, the plunger assembly 32 is in a retracted position so that it does not extend through or bypass any portion of the valve assembly 30. Accordingly, the valve assembly remains totally closed, thereby precluding any backflow of fluid from the patient through the device, while also precluding any air from gaining access to the patient's vascular system.

Figure 4:
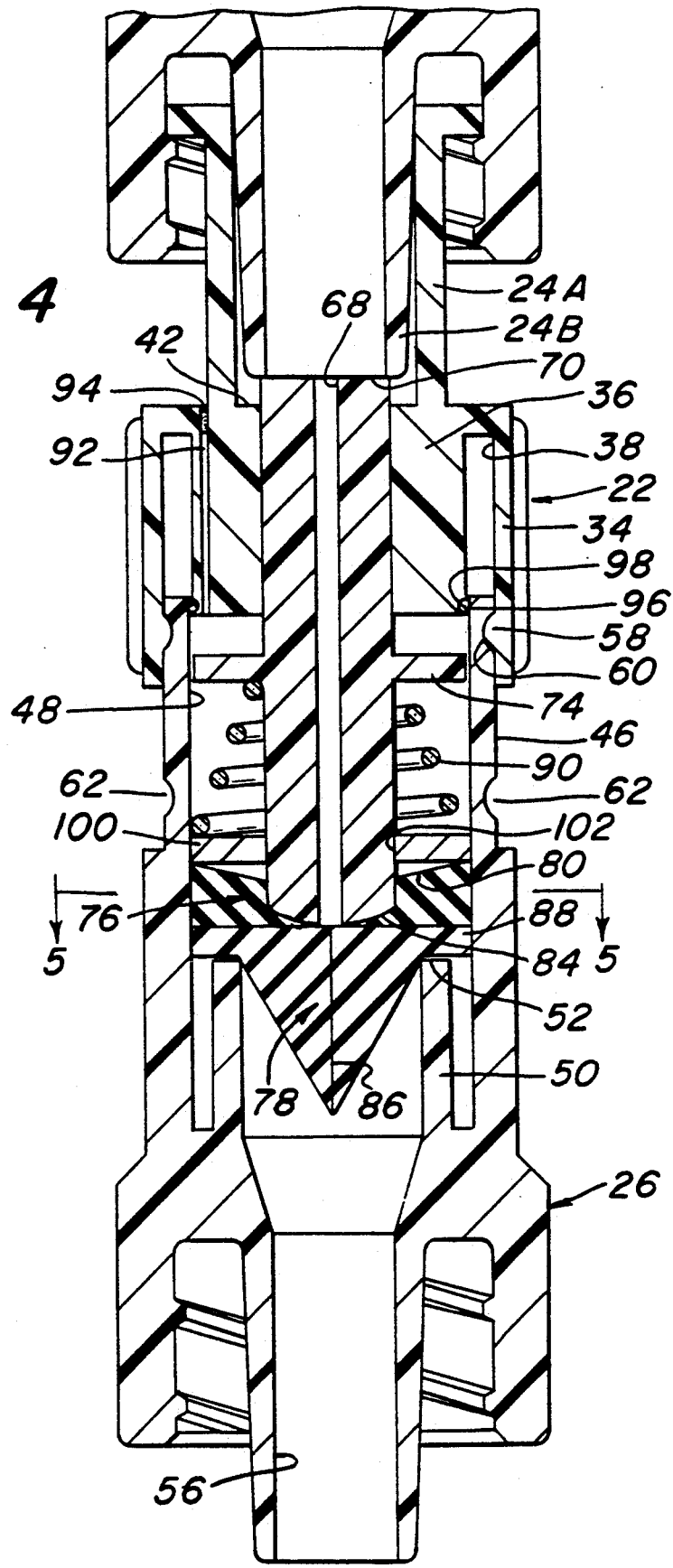
FIG. 4 is a longitudinal sectional view of the fluid shown in FIG. 1 in its partially opened state.

However, when the input line is connected to the luer fitting 24A, with the device 20 in the neutral position, such as shown in FIG. 4, the plunger assembly 32 is automatically extended from the retracted position to a partially extended position. In that position a portion of the plunger assembly extends through a portion of the valve assembly to effectively bypass that portion of the valve assembly. This action enables a fluid to be forced, e.g., injected from the input line, through the device 20 to the output line, and hence into the patient's vascular system, as will also be described later.

Once the fluid has been injected into the patient the input line may be disconnected from the input luer fitting 24A. This action results in the spring 90 carrying the plunger member 66 back to the retracted position, wherein its open end is located proximally of both valve elements 76 and 78. Accordingly, the device resumes its fully occluded condition.

Figure 6:
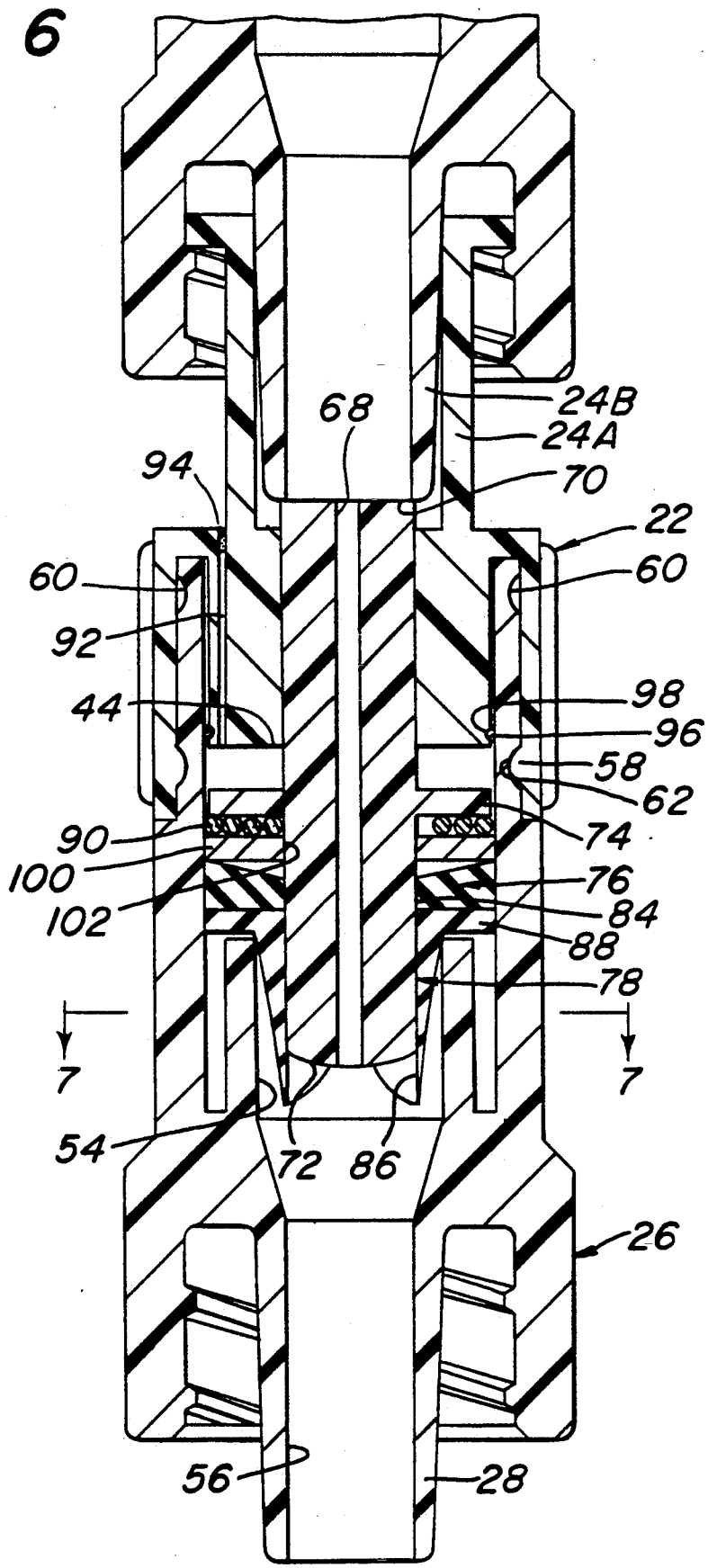
FIG. 6 is a longitudinal sectional view of the fluid shown in FIG. 1 in its fully opened state.

When an input line is connected to the input luer fitting 24A and the two housing sections 22 and 26 are pushed closer together from the neutral position to the actuated position, i.e., the annular ridge 58 of the housing section 22 is located within the annular recess 62 of the housing section 26, such as shown in FIG. 6, the plunger assembly is moved to its fully extended position wherein it extends fully through the valve assembly 30 to effectively bypass it. This action enables a fluid from the input line to flow to the output port and hence into the patient's vascular system. Since the valve is totally opened in this position the fluid, be it introduced under pressure from an injector or by a gravity feed from a bag, can flow at an increased flow rate into the patient through the device. Moreover, when the device 20 is in its actuated position a fluid sample can be readily taken from the patient by any suitable suction means connected to the input line.

Referring now to FIG. 1 the details of the plunger assembly 32 will now be considered. As can be seen therein that assembly basically comprises an elongated tubular plunger member 66 having a central passageway or bore 68 extending centrally through the entire length thereof. The proximal end of the plunger member 66 effectively forms a "cap" for engagement by the male luer fitting 24B when the input line is connected to the input luer fitting 24A, as will be described later. The distal end of the plunger member 66 is rounded at 72 to facilitate its selective passage through a pair of valve elements (to be described later) making up the valve assembly 30. An annular flange or stop 74 extends about the outer periphery of the plunger member 66 intermediate the distal and proximal ends of the plunger member.

The plunger member 66 is disposed within the central passageway 40 in the core 36 of the housing section 22 and is biased by a spring, to be described later, so that its cap 70 is spaced above the bottom surface 42 of the female luer fitting 24A, while its intermediate flange 74 is located abutting the front (proximal) surface 44 of the core 36 when the device 20 is in the neutral position (FIG. 1). The plunger member 66 is arranged to be moved against the bias of the spring, with respect to the housing section 22, from the retracted position to a partially extended position shown in FIG. 4, in automatic response to the connection of an input line to the input luer fitting 24A. In the partially extended position the plunger's cap 70 is disposed closer to the bottom surface of the female luer fitting 24A and its intermediate flange or stop 74 is spaced away from the front surface 44 of the core 36 of the housing section 22.

The plunger member 66 is also arranged to be manually moved along with the housing section 22 to a fully extended position when the device is in the "actuated" condition as shown in FIG. 6, as will also be described later.

The valve assembly 30 basically comprises a pair of valve elements 76 and 78. The valve element 76 is preferably a disk-like member, formed of any suitable resilient material, e.g., silicone, and having a conical proximal face 80 and a planar distal face 82. A normally closed elongated diametrically oriented slit 84 extends through the valve element 76 from the nadir of the proximal conical face 80 to the distal planar face 82. The valve element 78 is preferably a conventional a duck-bill valve, also formed of any suitable resilient material, and has a normally closed diametrically oriented slit 86 extending between its proximal and distal surfaces. An annular planar flange 88 surrounds the periphery of the duck-bill valve element 78 to support that element on the valve seat 52, with the duck-bill portion thereof extending into the passageway 54. The valve element 76 is disposed on top of (proximally) the duck-bill valve element 78.

As mentioned earlier the plunger member 66 is biased or loaded into its retracted position by a spring. That spring preferably comprises a helical compression spring 90. The spring 90 is disposed about the distal portion of the plunger member 66 distally of the annular flange 74 and is interposed between that flange and a washer 100. The washer 100 includes a central opening 102 through which the distal end of the plunger member 66 extends. The washer is disposed on top of (proximally) of the valve element 76. The spring 90 also serves to maintain alignment of the various internal components within the device 20.

An air evacuation passageway may optionally be included in the device 20, if desired. In particular, in a preferred embodiment of this invention that passageway comprises a small diameter bore extending longitudinally through the core 36 of the housing section 22. The passageway 92 communicates with the interior of the chamber 48 and with the ambient atmosphere outside of the device 20. A porous plug 94 is located at the proximal end of the passageway 92 to preclude any debris from entering through the passageway into the interior of the device 20.

In order to prevent any fluid from gaining egress out of the device 20 between its housing sections 22 and 26 an O-ring 96 is disposed within an annular recess 98 extending about the core 36 of the housing section 22. The cross sectional area of the O-ring is selected so that its outer surface abuts the inner surface of the sleeve 46, thereby forming a fluid tight seal between the housing sections in all operating positions of the device.

Operation of the device 20 is as follows: When the device is in the neutral position, such as shown in FIG. 1, its annular ridge 58 is snap-fit into the annular recess 60. If no input line is connected to its input port 24A, the spring 90 will have biased the plunger to the retracted position as shown therein. In this position the plunger's distal end 72 is located proximally of both valve elements 76 and 78, whereupon the slits 84 and 86, respectively, are closed. Accordingly, the device 20 is totally occluded so that fluid from the being's vascular system cannot flow out of the device, nor can air gain ingress into the being's vascular system. With respect to the latter, it should be noted that when the plunger member 66 is in its retracted position its intermediate flange 74 abuts the front face 44 of the core 36 of the housing section 22, thereby sealing the distal end of the air vent bore 92 and isolating the interior of the device from the ambient atmosphere.

When it is desired to introduce a fluid into the patient's vascular system an input line coupled to a source of such a fluid is connected to the input port fitting 24A, such as shown in FIG. 4. The housing sections are maintained with respect to each other in the neutral position by the annual ridge 58 remaining locked (snap-fit) within the annular recess 60. Accordingly, when the male luer fitting 24B on the input line is disposed within the female fitting 24A and secured thereto its distal end engages the cap 70 of the plunger member 66 to push the plunger member distally to the partially extended position against the bias of the spring 90. In this partially extended position the cap 70 of the plunger member engages the bottom surface 42 of the female luer fitting 24A. The plunger member 66 is of a predetermined length so that its rounded, open distal end 72 passes into and through the slit 84 of the valve element 76 and is closely adjacent the closed slit 86 of the duck-bill valve element 78, but does not enter it. Accordingly, only the valve element 76 is "opened" (i.e., bypassed by the plunger member 66). The device 20 is now ready to have a fluid forced, e.g., injected, therein via the input line. In particular, when the fluid is injected or otherwise forced under pressure into the input line, from means (not shown) it will flow through the inlet port, through the communicating passageway 68 in the plunger member 66 to the duck-bill valve element 78. The pressure of that fluid causes the duck-bill valve's slit 86 to open so that the fluid flows therethrough, through communicating passageway 54 to the outlet port, and from there through the outlet line into the vascular system of the being. Backflow of fluid from the patient's vascular system is precluded by the action of the duck-bill valve element 78. Moreover, air is precluded from gaining ingress into the being's vascular system since the interior chamber 48, which is now in fluid communication with the ambient atmosphere via the passageway 93, is never the less isolated from the fluid flow path through the device 20 by the plunger member 66.

In the event that a fluid is desired to be introduced at an increased flow rate into the being's vascular system, e.g., a fluid is to be provided from a gravity feed bag (not shown), the two housing sections 22 and 26 are slid closer together to the actuated position against the bias of the spring 90 (which is collapsed). To achieve that position the annular ridge 58 of the housing section 22 exits the annular groove 60 of the section 26 and enters and snap-fits within the annular groove 62. In this actuated condition (shown in FIG. 6) the distal end 72 of the plunger member extends through the slit 86 in the duck-bill valve element 78 as well as through the slit 84 in the valve element 76. Accordingly, the plunger member now extends through or bypasses both valve elements so that any fluid introduced into the input line flows readily through the plunger member's central passageway 68 to the passageway 54 and from there into the output line to the patient's vascular system.

As will be appreciated by those skilled in the art when the device is in the actuated position air is precluded from gaining ingress into the being's vascular system since the interior chamber 48, which is now in fluid communication with the ambient atmosphere via the passageway 92, is nevertheless isolated from the being's vascular system by the extending plunger member 66.

Sampling of a fluid from the patient's vascular system can be readily effected when the device is in the actuated position by merely coupling some fluid withdrawing device, e.g., a syringe, to the input line.

It should be pointed out at this juncture that the input and output ports need not be luer fittings, but can be any suitable fitting enabling the connection of input and output lines, respectively, thereto. Moreover, the snap-fitting locking mechanism of the ridge 58 and cooperating grooves 60 and 62, may be replaced by any suitable mechanisms, such as screw mechanisms or push-to-snap, push-to-release mechanisms. Further still, some means may be incorporated into the device to prevent its housing sections from being moved to the actuated position in the event that no input line is connected to the input port in order to ensure that air cannot gain ingress into the being's vascular system.

Without further elaboration, the foregoing will so fully illustrate our invention that others may, be applying current or future knowledge, adopt the same for use under various conditions of service.

We claim:

1. A device for providing fluid access to a portion of the vascular system of a being, said device comprising a housing means, valve means, and extendable plunger means, said housing means comprising a first housing section and a second housing section, said first housing section being coupled to said second housing section and being movable with respect to said second housing section from a first position to a second position and vice versa, said first housing section comprising first port means for connection to an input line, said second housing section comprising second port means for connection to an outlet line in fluid communication with said portion of the vascular system, said housing sections defining a hollow interior portion therebetween in which said valve means is located, said valve means comprising a first openable aperture and a second openable aperture, said extendable plunger means comprising a tubular member movably coupled to said first housing section for extension through said first openable aperture in response to said input line being connected to said first port means when said first housing section is in said first position, whereupon said a fluid may be forced from said input line through said tubular member and through said second openable aperture into said output line, said tubular member being retracted out of said first openable aperture in response to the disconnection of said input line from said first port, whereupon said first and second port means are isolated from each other by said valve means.

2. The device of claim 1 wherein the movement of said first housing section to said second position with said input line connected to said first port means causes said tubular member to extend through both of said openable apertures, whereupon said first and second port means are in fluid communication with each other via said tubular member.

3. The device of claim 2 wherein said first port means comprises a luer fitting.

4. The device of claim 2 wherein said second port means comprises a luer fitting.

5. The device of claim 3 wherein said second port means comprises a luer fitting.

6. The device of claim 1 additionally comprising spring biasing means coupled to said tubular member to retract said, tubular member out of said first openable aperture when said input line is disconnected from said first port means.

7. The device of claim 2 additionally comprising spring biasing means coupled to said tubular member to retract said tubular member out of said first openable aperture when said input line is disconnected from said first port means.

8. The device of claim 1 additionally comprising detent means to hold said first and second housing sections in either of said first or second positions.

9. The device of claim 2 additionally comprising detent means to hold said first and second housing sections in either of said first or second positions.

10. The device of claim 1 wherein said valve means comprises a first and second resilient valve members, said first valve member being a disk-like member having said first openable aperture therein, said second valve member being a duck-bill member whose openable aperture comprises a slit.

11. The device of claim 2 wherein said valve means comprises a first and second resilient valve members, said first valve member being a disk-like member having said first openable aperture therein, said second valve member being a duck-bill member whose openable aperture comprises a slit.

12. The device of claim 6 wherein said valve means comprises a first and second resilient valve members, said first valve member being a disk-like member having said first openable aperture therein, said second valve member being a duck-bill member whose openable aperture comprises a slit.

13. The device of claim 8 wherein said valve means comprises a first and second resilient valve members, said first valve member being a disk-like member having said first openable aperture therein, said second valve member being a duck-bill member whose openable aperture comprises a slit.

14. The device of claim 1 additionally comprising air vent means in fluid communication with said hollow interior portion.

15. The device of claim 1 wherein said air vent means is selectively sealed by said plunger means when no input line is connected to said first port means.

* * * * *